United States Patent [19]

Belot

[11] 4,455,423

[45] Jun. 19, 1984

[54] PROCESS FOR THE MANUFACTURE OF CYANURIC ACID BY HEATING UREA AT A TEMPERATURE ABOVE ITS MELTING POINT

[75] Inventor: Jean Belot, Toulouse, France

[73] Assignee: CdF Chimie S.A., Paris, France

[21] Appl. No.: 432,872

[22] Filed: Oct. 5, 1982

[30] Foreign Application Priority Data

Mar. 24, 1982 [FR] France ................................ 82 04960

[51] Int. Cl.³ .......................................... C07D 251/32
[52] U.S. Cl. .................................................. 544/192
[58] Field of Search ........................................ 544/192

[56] References Cited

U.S. PATENT DOCUMENTS 3,236,845 2/1966 Baskin .

FOREIGN PATENT DOCUMENTS

| | | |
|---|---|---|
| 1183672 | 7/1959 | France . |
| 1229102 | 9/1960 | France . |
| 1336672 | 7/1963 | France . |
| 1346599 | 11/1963 | France . |
| 2091660 | 12/1971 | France . |
| 2090817 | 12/1971 | France . |
| 2246554 | 10/1974 | France . |

Primary Examiner—John M. Ford
Attorney, Agent, or Firm—Millen & White

[57] ABSTRACT

In a process for the manufacture of cyanuric acid by heating urea at a temperature above its melting point, an aqueous solution of urea is sprayed onto granules of crude cyanuric acid, recycled externally, and heated at a temperature of 220°–280° C. in a heat exchange zone heated by the walls thereof. A rotor in the device comprising a tubular shaft on which hollow discs are mounted, and in which a heat-transfer fluid circulates, is also employed to heat the material to the manufacture cyanuric acid in high yields.

11 Claims, 2 Drawing Figures

PROCESS FOR THE MANUFACTURE OF CYANURIC ACID BY HEATING UREA AT A TEMPERATURE ABOVE ITS MELTING POINT

BACKGROUND OF THE INVENTION

This invention relates to a process for the manufacture of cyanuric acid by heating urea at a temperature above its melting point, and recycling cyanuric acid granules, with urea adsorbed thereon in a heat exchange zone and heating to a predetermined temperature.

It is known in the prior art to manufacture cyanuric acid by heating urea to a predetermined temperature above its melting point. Cyanuric acid, i.e., $C_3N_3O_3H_3$, exists in two tautomeric forms as follows:

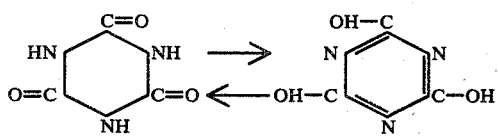

The thermal decomposition of urea into cyanuric acid in either form follows the reaction

Other side reactions also occur and result in the formation of ammelide, amidine and guanidines.

The prior art manufacture of cyanuric acid from urea based upon the above-discussed reaction is generally conducted in two stages. The first stage involves taking molten urea, or urea in aqueous solution, adsorbed on granules of crude cyanuric acid which had been prepared beforehand and heating to a temperature of 220°–280° C. The granules impregnated with urea are recycled numerous times, typically 5–9, to achieve maximum conversion of urea for production of cyanuric acid.

The second stage of the process is a purification of the crude cyanuric acid by treating with a strong acid, in dilute solution, such as sulfuric acid, phosphoric acid, or preferably, nitric acid.

This type of prior art process is generally described in French Pat. Nos. 1,183,672 and 1,229,102 wherein cyanuric acid granules impregnated with sprayed urea are passed through a heat exchange zone such as rotary furnace, or trough containing paddles, or an endless screw, or other conveying means. Heat of reaction is supplied externally by, for example, radiant heat panels or natural gas burners. A portion of the stream is then recycled into the furnace for further treatment. Typically, the crude cyanuric acid is taken up in a conveyor and directed into a hopper with a sieve, in which fine granules are separated from coarse granules and the coarse granules ground into fine granules. By fine granules is meant granules no greater than 12.5 mm, with particles larger than this being considered coarse granules, more preferably, the fine granules are 1.9–12.5 mm in size. The fine granules and the ground coarse granules are then reintroduced into the top of the zone.

However, a problem with this prior art method is that if the cyanuric acid, which is at a temperature of about 220° C., is directly recycled, the zone surfaces foul up rapidly and the installation is brought to a standstill.

Previously, this problem has been solved by cooling the granules and spraying with water before recycling. Typically, about 2000 kg/hr of cyanuric acid is treated with 80 to 100 l/day of sprayed water before recycling to lower the temperature thereof to about 180° C. The water spraying improves the adsorption capacity of the granules to the urea solution. More specifically, without water spraying the porosity of the granules, measured by the mercury porosity standard, is 12–15% as compared to with water spraying wherein a porosity of about 27% is achieved.

On the other hand, the addition of water results in a number of disadvantages. More specifically, energy consumption increases because of lowering of the temperature by the water, as well as the fact that the water must subsequently be removed. Furthermore, condensation occurs in the hoppers used for sieving, and in one attempt to solve this problem of condensation the covers of the hoppers were opened, but this resulted in a high emission of irritant dusts.

SUMMARY OF THE INVENTION

It is thus an object of the invention to provide an improved process for the production of cyanuric acid by the heat treatment of urea in a heat exchange zone wherein recycling of crude cyanuric acid for further heat treatment is without cooling thereof, and without fouling of the installation.

Another object of this invention is to provide a method of treating urea to produce cyanuric acid wherein the temperature in the heat treatment zone is more accurately controlled resulting in a more efficient process with reduced energy consumption, and with thermal decomposition of cyanuric acid due to localized overheating virtually eliminated.

Still another object of the invention is to provide an improved process wherein formation of coarse particles is substantially reduced, and whereby the sorting means normally required for sorting the coarse granules from the fine granules can be eliminated.

Yet still another object is to provide an improved process for increasing the yield of cyanuric acid, as compared to the prior art process, whereby a smaller installation can be employed.

Upon further study of the specification and appended claims, further objects and advantages of this invention will become apparent to those skilled in the art.

In accordance with the invention an improved process is provided for producing cyanuric acid wherein the heating of the urea impregnated granules is conducted in a zone having a heating rotor comprised of a tubular shaft having heating discs mounted thereon. The heating of the urea impregnated cyanuric acid granules to a temperature of about 220°–280° C., preferably 260° C. is conducted both with the heated inner walls of the zone as well as with the heating rotor. Thus, in accordance with this process, a more uniform temperature of the urea impregnated cyanuric acid granules is achieved. Likewise, the resulting adsorption capacity of the granules to the urea is greater without requiring water spraying before recycle, and formation of coarse granules is substantially reduced.

In a preferred aspect, the heating rotor is a tubular shaft with hollow discs whereby heating is conducted by circulating a heat transfer fluid in the tubular shaft and in the hollow discs.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein.

DETAILED DISCUSSION OF THE INVENTION

Figure 1:
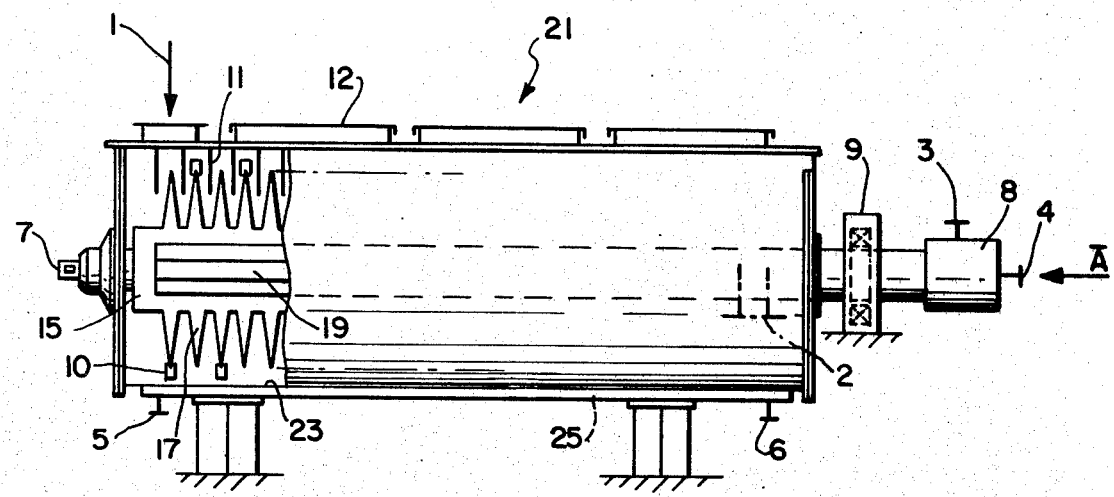
FIG. 1 is a side view, in partial section, of the apparatus for conducting the process according to the invention.
Figure 2:
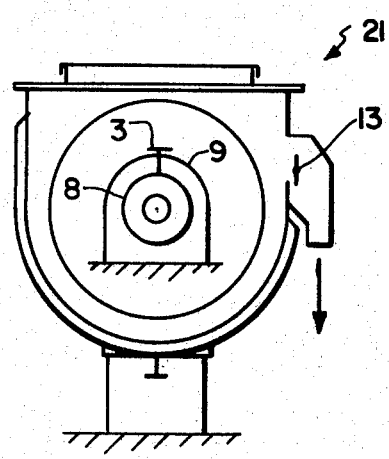
FIG. 2 is an end view, in the direction of arrow $\overline{A}$, of the apparatus shown in FIG. 1.

The apparatus employed for conducting the process according to the invention is generally illustrated in FIGS. 1 and 2. Other apparatuses of the type capable of use in the process according to the invention are described in French Pat. Nos. 2,090,817 and 2,091,660, the disclosures therein being incorporated by reference herein.

As shown in FIG. 1, the device is a heat exchange zone comprising a rotoreactor 21 or trough having a tubular rotor 15 with hollow discs 17 extending outwardly perpendicularly therefrom. The center of the rotor 15 is arranged to form a double envelope type structure 19 whereby a heating fluid can be passed thereinto and to the discs in a circulating pattern as will become evident to those skilled in the art. Typically, this device will be in a horizontal position for generally horizontal flow therethrough.

The rotor 15 is driven at a drive connection 7 by a conventional drive or motor arrangement (not shown). Preferably, this driving arrangement is variable in speed of rotation. At the other end the rotor 15 is mounted for rotation on bearing 9 and has a rotating joint 8 with an inlet 3 for heating fluid flow into the rotor 15 and an outlet 4 for the heating fluid flow out from the rotor 15.

The interior of the rotoreactor 21 includes scraper blades 10 attached to the ends of the discs 17 and adjustable in orientation in a conventional manner to scrape materials of the inner walls 23. Furthermore, combs 11 are provided and arranged in a manner so as to engage and cooperate with the rotating discs 17 to ensure movement of material through the rotoreactor 21.

The inner walls 23 of the rotoreactor 21 also include an envelope arrangement 25 with an inlet 5 and an outlet 6 for providing a heating fluid thereto to heat the inner walls 23 of the rotoreactor 21. The heating fluid passed through the envelope arrangement 25 can be the same as that passed through the rotor 15, and is conventional and well known to those skilled in the art. For example, one such fluid can be the heating fluid sold by RHONE-POULENC under the tradename GILOTHERM. More generally, the heat transfer fluid will preferably consist of a mineral oil or other stable chemical compound or mixtures having a low vapor pressure at temperatures employed.

When conducting the process, the material, i.e., cyanuric acid granules impregnated with urea are fed through the rotoreactor 21 for treatment therein by means of inlet 1, and the treated product is removed by means of outlet 2.

FIG. 2 illustrates an end view of the device of FIG. 1 looking in the direction indicated by the arrow $\overline{A}$, i.e., from the bearing 9 side. The outlet 2 for the material is more clearly shown having an adjustable outlet valve 13 by means of which the flow of material through the rotoreactor 21 can be controlled. Regulation of the valve is conventional and the control mechanism is not shown. Furthermore, not shown is a recycle means whereby a partial stream of the exiting material can be recycled to the inlet 1 after being impregnated with urea.

In addition to the above-discussed elements, the device also includes inspection ports 12 which can be opened to inspect the condition of the reactor 21 to ensure that there is no fouling or clogging occurring. Likewise, repair or maintenance operations can be conducted on the reactor 21 through these ports 12.

In operation, when such a device is employed it has been found that for every 1.8 tons of urea yields about 1 ton of pure cyanuric acid, regardless of whether or not water is sprayed on the recycled crude cyanuric acid. Furthermore, a porosity of the granules of about 27%, measured using mercury, can be maintained even without water spray.

In conducting the process, the heating surfaces need be only raised only to a temperature of about 320°-330° C. to obtain a temperature of 260° C. in the bed because of the increased heating capacity provided by the heating rotor 15. This compares very favorably with the process when conducted in a conventional rotoreactor 21 or trough employing radiant heat panels which requires that the inner walls of the trough be heated to 450°-600° C. in order to obtain the same temperature as above in the bed. Thus, since the heating surfaces according to the process of the invention are at a closer temperature to that of the bed, localized overheating is avoided and thus, partial decomposition of the cyanuric acid as a result is also avoided thereby resulting in a higher proportion of cyanuric acid in the end product obtained.

In accordance with the invention, the surfaces of the heating rotor provide at least 50% of the heat supply and can provide up to 95% of it. For example the total heat surface can vary from 3 $m^3$ to about 300 $m^2$ according to the number of rotors, and length and to the number and the diameter of discs.

Without further elaboration, it is believed that one skilled in the art can, using the preceding description, utilize the present invention to its fullest extent. The following preferred specific embodiment is, therefore, to be construed as merely illustrative, and not limitative of the remainder of the disclosure in any way whatsoever. In the following example, all temperatures are set forth uncorrected in degrees Celsius; unless otherwise indicated, all parts and precentages are by weight.

EXAMPLE

The heat treatment of urea is carried out in a zone having a volume of 2.8 $m^3$ and a cyanuric acid capacity of 800 kg. The zone is heated by a heating rotor having a total exchange surface of 25 $m^2$, and by an inner wall of the zone having an exchange surface of 7 $m^2$. The heat-transfer fluid for heating is the abovediscussed product sold under the tradename GILOTHERM by RHONE-POULENC. The heat-transfer fluid is introduced at a temperature of 330° C. The heating rotor has 48 discs and 49 adjustable scrapers, and is caused to rotate at a speed of 32 rpm.

1,500 kg per hour of crude cyanuric acid, which is recycled by external recycling and is at a temperature of 230° C., are introduced into the trough. The crude cyanuric acid is impregnated with 466 kg/hour of 75% strength urea solution.

Under these conditions, the production of crude cyanuric acid is 256 kg/hour, which corresponds to a production of 236 kg/hour of pure cyanuric acid. The crude cyanuric acid contains less than 0.4% of urea.

The preceding example can be repeated with similar success by substituting the generically or specifically described reactants and/or operating conditions of this invention for those used in the preceding example. From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the manufacture of cyanuric acid by heating urea at a temperature above its melting point, the process comprising spraying one of melted urea or a concentrated solution of urea onto cyanuric acid granules, conducting the urea adsorbed on cyanuric acid granules through a heat exchange zone with heated inner walls wherein the urea impregnated granules are heated to a temperature of 220°–280° C., and wherein a recycle of a partial stream of cyanuric acid granules is conducted with water spraying on the granules before the recycle, said partial stream of granules being again sprayed wth one of melted urea or a concentrated solution of urea and conducted impregnated with urea into the heat exchange zone, the improvement comprising conducting the heating of the urea-impregnated granules through a heat exchange zone containing a heating rotor constituted by a tubular shaft having hollow discs fixedly secured thereto in a manner such that a heat transfer fluid is circulated through both said rotor and said discs to effect the heating, and eliminating the water spraying on the granules before the recycle, whereby a more uniform temperature of the urea impregnated cyanuric acid granules in the zone, greater adsorption capacity of the cyanuric acid granules to the urea, and elimination of formation of coarse cyanuric acid granules is achieved.

2. A process according to claim 1 further comprising conducting the process in a heat exchange zone having combs operatively associated with said rotor, the rotor having heat exchange discs fixedly secured thereto, and said combs secured to the inner walls of the zone, and said discs moving said urea impregnated granules in one direction through said zone.

3. A process according to claim 1, wherein said heating rotor is hollow, and comprising conducting said heating by circulating a heat transfer fluid in said rotor.

4. A process according to claim 2, wherein said heating rotor and discs are hollow, and comprising conducting said heating by circulating a heat transfer fluid in said rotor and discs.

5. A process according to claim 1, wherein adjustable scraping means are fixed to the outer ends of said rotor heat exchange surfaces, and comprising scraping material off the inner walls of the heat exchange zone by means of said scraping means.

6. A process according to claim 2, wherein adjustable scraping means are fixed to the outer ends of said rotor discs, and comprising scraping material off the inner walls of the heat exchange zone by means of said scraping means.

7. A process according to claim 3 comprising introducing said heat transfer fluid at a temperature of 330° C. to heat the material in the heat exchange zone to a temperature of 260° C.

8. A process according to claim 3, wherein the outer walls of the zone are also hollow and further comprising conducting said heating by introducing said heat-exchange fluid into the hollow outer walls of the zone.

9. A process according to claim 1 comprising conducting the process in said heat exchange zone, the latter further comprising combs operatively associated with said heating rotor for engaging and cooperating with said discs to ensure movement of the material through the zone.

10. A process according to claim 1 further comprising scraping material adhered to the walls of the zone by means of scraping means fixed to the outer ends of said hollow discs.

11. A process according to claim 1 comprising maintaining the temperature of heating surfaces exposed to the urea-impregnated granules to about 320°–330° C. to raise the temperature of the granules to about 260° C.

* * * * *